United States Patent [19]
Klingenstein

[11] Patent Number: 6,013,023
[45] Date of Patent: *Jan. 11, 2000

[54] FECAL INCONTINENCE DEVICE AND METHOD

[76] Inventor: R. James Klingenstein, 151 Tremont St. Apt 23 E., Boston, Mass. 02111

[*] Notice: This patent issued on a continued prosecution application filed under 37 CFR 1.53(d), and is subject to the twenty year patent term provisions of 35 U.S.C. 154(a)(2).

[21] Appl. No.: 08/889,394

[22] Filed: Jul. 8, 1997

Related U.S. Application Data

[63] Continuation of application No. 08/791,282, Jan. 30, 1997.

[51] Int. Cl.⁷ ............................................. A61F 2/00
[52] U.S. Cl. ................................ 600/29; 600/31; 600/32
[58] Field of Search .................... 128/885, 887, 128/DIG. 25; 600/29, 30, 31, 32

[56] References Cited

U.S. PATENT DOCUMENTS

| | | |
|---|---|---|
| 1,282,881 | 10/1918 | Landis . |
| 4,686,985 | 8/1987 | Lottick . |
| 5,545,176 | 8/1996 | Murtfeldt ................................ 606/192 |
| 5,603,685 | 2/1997 | Tutrone, Jr. ................................ 600/26 |
| 5,702,421 | 12/1997 | Schneidt ................................ 600/32 |

FOREIGN PATENT DOCUMENTS

0068318 A1  1/1983  European Pat. Off. .......... A61F 5/44

OTHER PUBLICATIONS

Cerulli MA et al. (1979), Progress in biofeedback conditioning for fecal incontinence, Gastroenterology 76:742–746.

Christiansen J. et al. (1989), Implantation of artificial sphincter for anal incontinence. Report of five cases, Dis. Colon Rectum 32:432–436.

Madoff R.D. et al. (1992), Fecal incontinence, N. Engl. J. Med. 326:1002–1007.

*Primary Examiner*—John P. Leubecker
*Assistant Examiner*—R. Kearney
*Attorney, Agent, or Firm*—Testa, Hurwitz & Thibeaut, LLP

[57] ABSTRACT

Provided is a device to control fecal incontinence and methods for its use. The device comprises a longitudinal tubular member having attached thereto bilaterally-extending wings for securing the device while in use. The device also comprises an expandable portion for prevention of unwanted defecation during use of the device.

16 Claims, 2 Drawing Sheets

FECAL INCONTINENCE DEVICE AND METHOD

This is a continuation of copending application Ser. No. 08/791,282 filed on Jan. 30, 1997.

FIELD OF THE INVENTION

The invention relates to fecal continence devices and methods which permit comfortable sitting, standing, and walking. Devices and methods of the invention are useful for treating fecal incontinence.

BACKGROUND OF THE INVENTION

Fecal incontinence typically is a source of physical discomfort and the cause of social and personal debilitation. It is most likely to affect the aged or individuals suffering from neurological trauma. However, abnormalities in stool volume or consistency, colonic transit, anal sphincter function, anorectal sensation, or anorectal reflexes also may result in incontinence. Madoff, et al., *New Eng. J. Med.,* 326: 1002–1007 (1992). Finally, a significant number of incontinence cases involve post-partum pelvic neuropathies, and thus may affect women at a relatively young age. Many of these women develop loose pelvic floor muscles and a more flaccid recto-vaginal septum.

Mild cases of fecal incontinence typically are treated by instituting dietary changes. Biofeedback therapies also have been proposed in which a balloon, inserted in the rectum, provides a sensation similar to that of stool immediately prior to voiding. The patient is trained to perceive differing volumes of distention in the balloon and to respond accordingly by contracting and relaxing the anal sphincter muscles. See, e.g., Cerulli, et al., *Gastroenterology,* 76: 742–746 (1979).

Surgical remedies for severe cases of fecal incontinence include sphincter repair, placation of the posterior sphincter, anal encirelement in which a metal or elastic band mechanically tightens the anus, and muscle transfer procedures. Each of these techniques attempts to create a passive barrier to stool. However, they typically produce poor results, including leakage of stool, infection, and fecal impaction.

Recently, it has been proposed that fecal incontinence that cannot be corrected by surgery or by other approaches may be treated by insertion into the rectum of an artificial anal sphincter consisting of an inflatable cuff. Christiansen, et al., *Dis. Colon Rectum,* 32: 432–436 (1989). The cuff may be manually controlled in order to regulate passage of stool. Still other devices for control of fecal incontinence have been proposed. For example, U.S. Pat. No. 4,850,986 reports a fecal incontinence device that includes a tube inserted in the rectum and held by an adhesive or a clip to the thigh. Fecal incontinence bags have also been reported as a means of collecting voided stool. Such bags generally include a portion that is inserted in the rectum and connected to a disposable collection bag. See, e.g., U.S. Pat. No. 4,917,692.

A problem with such non-surgical devices for controlling fecal incontinence is that they are intrusive and often make walking, sitting, and other activities difficult. Moreover, such devices are not easily controlled in order to allow voiding of stool when desired by the patient. Accordingly, there is a need in the art for means for controlling fecal incontinence that is convenient, relatively non-intrusive on daily physical activity, and easy to regulate and manipulate during use. Such means are provided by the present invention.

SUMMARY OF THE INVENTION

The invention provides devices for controlling fecal incontinence and methods for their use. Generally, a device of the invention is inserted into the vagina and causes the recto-vaginal septum to deviate, thereby occluding the rectal canal. Such a device preferably comprises an expandable or deformable member or body for insertion into the vagina of a patient. Upon insertion, the device displaces the recto-vaginal septum dorsally, thereby occluding the lumen of the rectum. The expandable member may have attached thereto a pair of bilaterally-extending wings, which may be detachable, that conform to the surface of the buttocks of a patient, thereby to maintain the position of the device in the vagina. It is preferred that the wings are flexibly attached to the member in order to adapt to the size of the patient's buttocks. Also in a preferred embodiment, the invention provides a device comprising a substantially tubular member for insertion into the vagina of a patient, the tubular member having an expandable portion capable of assuming a first, unexpanded position, and a second, expanded position. In the second position, the expandable portion exerts a force on the recto-vaginal septum, causing a deviation of the septum into the rectal canal. Sufficient force causes a complete occlusion of the rectal canal.

In a preferred embodiment, a device according to the invention comprises a member formed for insertion in the vagina, and having an expandable portion. The member, in a preferred device according to the invention, is comprised of a biocompatible material, preferably, plastic, latex, polyurethane, rubber, a polystyrene polymer or copolymer or any combination of the above.

The expandable portion causes the recto-vaginal septum to deviate dorsally into the rectal canal. This results in compression on the lumen of the terminal rectum. In a preferred device, the expandable portion is oriented longitudinally or horizontally along the top or posterior (meaning nearest the spine), aspect of the device. The expandable portion comprises a flexible material, such as an expandable sheath. The invention contemplates a spectrum of member shapes including but not limited to, tubular, disc, U, and ring shapes. It is contemplated that the shaped member may be solid or hollow.

In a preferred embodiment, a device according to the invention comprises a hollow tubular member having an expandable or inflatable sheath. The sheath defines a fully-enclosed space surrounding a portion of the member having at least one opening communicating between the hollow portion of the member and the space defined by the sheath. Accordingly, when a gas or a fluid is forced through the member, the sheath expands in accordance with the volume of gas or fluid as the gas or fluid enters the space defined by the sheath via the opening. A valve preferably is fixed at the distal (near natural body orifices) end of the device, such that it is accessible, but not intrusive against sitting, standing, or walking. The valve is, therefore, preferably recessed such that its opening is flush with the vaginal orifice.

Also in a preferred embodiment, a device of the invention comprises a hollow tubular member comprising a closed end and an open end, and further comprising a sheath that defines an enclosed space surrounding at least a portion of the member; wherein the member contains at least one opening that communicates between the hollow portion defined by the member and the enclosed space created by the sheath. A preferred device further comprises a valve connected to the open (distal) end of the member. The valve is capable of receiving means for inflating the sheath as, for example, a syringe, a pump or other device for forcing gas or liquid through the hollow portion of the member. If the hollow member is itself inflatable or expandable, the valve is attached to the open end of the member and is capable of receiving means for directly inflating the member.

Also in a preferred embodiment, a device according to the invention comprises a locking valve for prevention of backflow of material introduced to inflate the member or the sheath and for releasing such material when desired in order to remove the device from the patient. In a preferred embodiment, a pump is removably attached to the valve.

A preferred device according to the invention is comprised of a biocompatible material, preferably plastic, latex, polyurethane, rubber, a polystyrene polymer or copolymer, or any combination of the above. In any case, the device is sufficiently flexible so as not to impede sitting, standing, or walking. For example, the member may be collapsible to aid in sitting, such that an uninflated portion of the member collapses upon sitting. Alternatively, walls of the member may be sufficiently thin so as to not be intrusive. Methods of the invention comprise inserting a device, as describes above, into the vaginal cavity to deviate the recto-vaginal septum.

A use of the device comprises inserting the device into the vagina of a patient and increasing the diameter of the device, or preferably a portion thereof, by, for example, forcing gas or liquid through the member or a portion thereof or releasing a retractable fin to increase the diameter of the device. For purposes of the invention, the term "tubular" means a generally cylindrical shape that may be comfortably inserted into the vagina of a patient. As such oblong, rectangular, or other shapes with rounded edges are contemplated. Other contemplated shapes that may be comfortably inserted are ring, disc and U shapes.

Numerous additional features and advantages of the invention will become apparent upon consideration of the following detailed description thereof.

DETAILED DESCRIPTION OF THE INVENTION

The invention provides a device for controlling fecal incontinence. The device is preferably constructed of a soft, flexible, biocompatible material, such as plastic, rubber, or a synthetic compound, such as a styrene-butadiene copolymer. The size of the device may be varied to fit an individual patient.

A device of the invention provides an impedance in the rectum to unwanted defecation, while providing maximum comfort and flexibility for walking and sitting. Increased wearing comfort is achieved through the use of a soft, biocompatible material for insertion into the patient's vagina. Preferably, a portion of the device oriented on the posterior aspect of the member in the vagina is inflated, while the rest of the device remains uninflated. However, it is also possible for the entire device to be inflated. A valve for introduction of gas or liquid for inflation of the device, or portion thereof, is preferably situated near the vaginal opening so as to provide access for inflation. However, the valve is as unobtrusive as possible to sitting, standing, or walking (i.e., it does not protrude unnecessarily). In a preferred embodiment, the device comprises an attached balloon or sheath at its mid-section. The sheath is attached, as described below, to an outer surface of the member with apertures communicating from an inner hollow chamber defined by the member to an enclosed space defined by the sheath. The sheath is inflated by forcing gas or liquid through the device, wherein gas or liquid inflates the sheath by passing through the apertures. By using a locking valve, the device may be maintained in an inflated state until the patient desires to remove the device, at which time the sheath is deflated.

Figure 1:
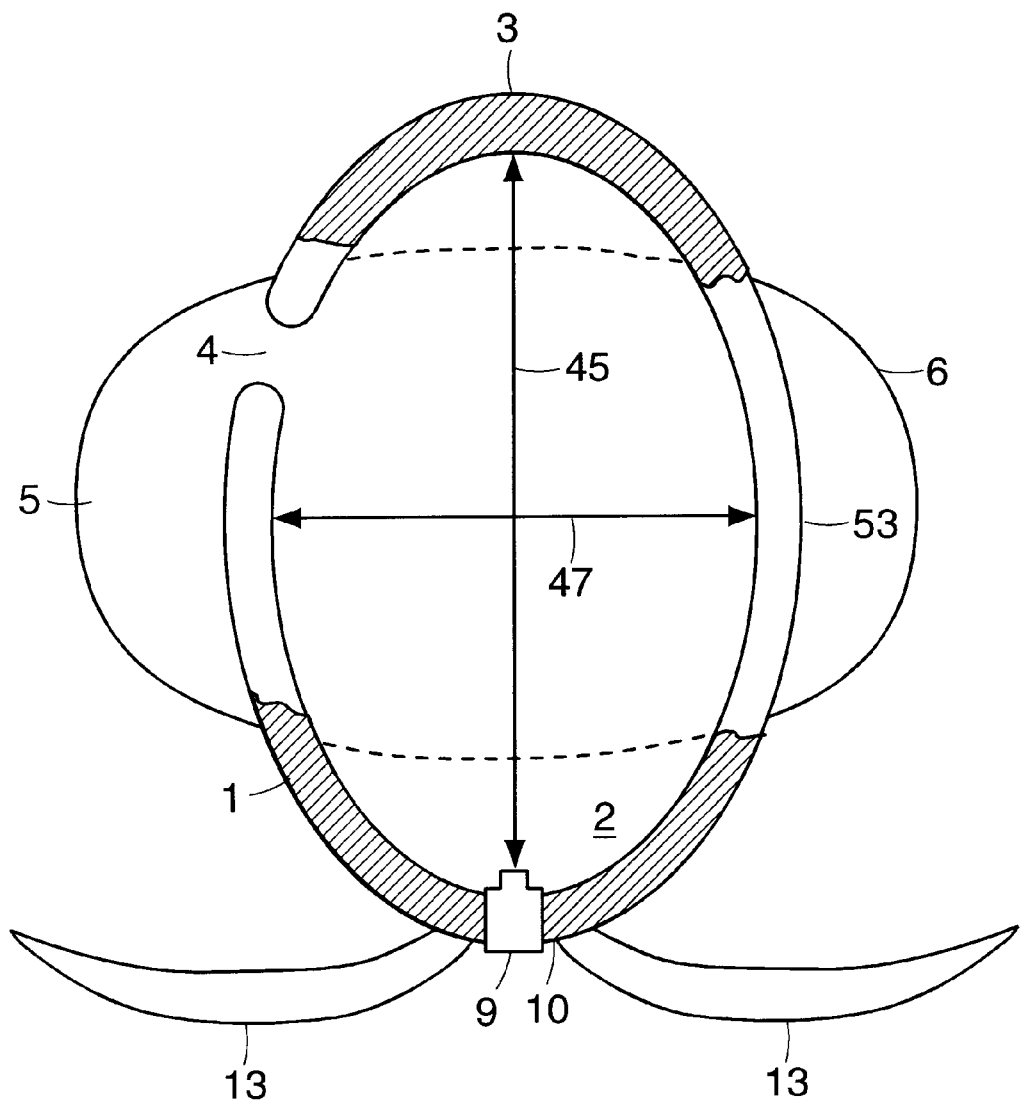
FIG. 1 is a sagittal section through a device according to the invention. The device is oval. The Figure shows an inflated sheath 6 at the midsection of member 1 as would be the case when the device has been inserted for use. Broken shading in the Figure is for convenience in showing the region enveloped by the sheath.

A preferred device for intra-vaginal use is shown in FIG. 1; wherein a hollow, tubular member 1 defines a longitudinal cavity 2 that terminates in a closed proximal end 3, which is preferably a rounded end for easy insertion in a patient. The hollow member is any shaped member that conforms to the vaginal cavity including but not limited to, tube, disc, u- and ring shapes. Near the closed proximal end 3, an opening 4 allows communication between the longitudinal cavity 2 and an enclosed space 5 created by an expandable sheath 6 that is disposed completely or partially around the circumference of a portion of the tubular member 1 near the mid-section 53 of the tubula member. The sheath 6 is constructed of a flexible material capable of being inflated. A valve 9 is installed at the open distal end 10 of the tubular member, the valve being capable of receiving a removable means (not shown) for expanding the sheath 6. Such means may be a syringe, a pump, or other pumping means which forces a gas, for example air, or a liquid, for example saline, through the longitudinal cavity 2 of the tubular member and further through the opening 4 into the interior space 5 so as to expand the sheath 6 to create a balloon (i.e., an inflated sheath). The valve 9 is preferably a locking valve, such as a Bardex®5 cc Luer Lock valve. Accordingly, upon introduction of gas or liquid into the cavity 2, the valve locks, causing the sheath to remain expanded. The expanded sheath, aids in securing the device in the vagina between the cervix, proximally, and the vaginal sphincter, distally. Intra-rectal use of this device is also contemplated and was disclosed in co-owned, co-pending U.S. patent application Ser. No. 08/791,282 and incorporated by reference, herein.

As an intra-vaginal device, the removable, bilateral wings 13 at or near the open (distal) end 10 of the member are optional. Cranial (forward) migration of the device into the uterine body is prevented by the cervix in most patients or by the vaginal cuff in a hysterectomized patient. The wings may assist in holding the device firmly in place to ensure predictable compression of the rectum. The wings may extend anteriorly and posteriorly to assist in holding the device in place. If used, the wings are preferably made of a soft biocompatible material and are flexible so as to conform to the buttocks and/or thighs of the patient in whom the device is installed. The wings cause the device to remain in place so as to maintain a proper seal between the ballooned sheath and the wall of the vagina, thus ensuring that the expanded intra-vaginal device is appropriately positioned to displace the recto-vaginal septum, thereby compressing the rectal lumen. An adhesive may be attached to an inner surface of the wings in order to aid attachment of the wings to the buttocks or abdomen of the patient. The wings should be flexibly attached to the tubular member in order not to impede sitting, standing, or walking.

Use of the intra-vaginal device comprises inserting the closed end portion of the member into the vagina so that the closed end of the member approaches the cervix. The device may be pre-lubricated or a lubricant may be applied prior to insertion in order to aid in the insertion of the device. The valve should extend to at least the vaginal opening in order to allow insertion of the expanding means (e.g. a syringe) into the valve for inflation of the sheath. The sheath is expanded to cause the recto-vaginal septum to deviate posteriorly (towards the spine), thereby, compressing the lumen of the terminal rectum. Ideally, similar to a contraceptive intravaginal diaphragm, the patient should not feel the expanded sheath. The device should be expanded sufficiently to prevent displacement from the vaginal cavity. Once expanded, the pumping means is removed. When defecation is desired, the device is deflated by allowing the liquid or gas to escape the ballooned portion of the member, for example, by reinsertion of the pumping means causing the sheath or inflated portion of the tubular member to deflate. The device may also be deflated, if necessary, to allow urination.

Figure 2A:
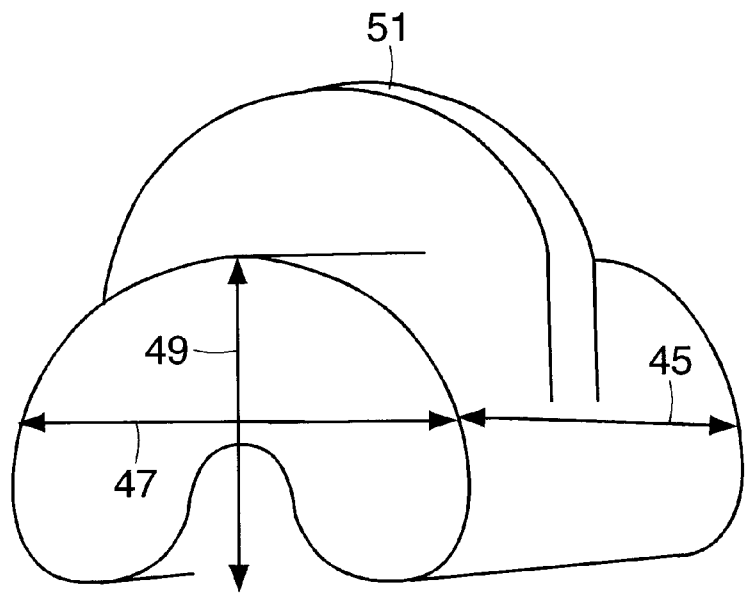
FIG. 2A is a transverse view through a device of the invention showing a flexible or expandable portion in an horizontal upright position. The member is u-shaped.
Figure 2B:
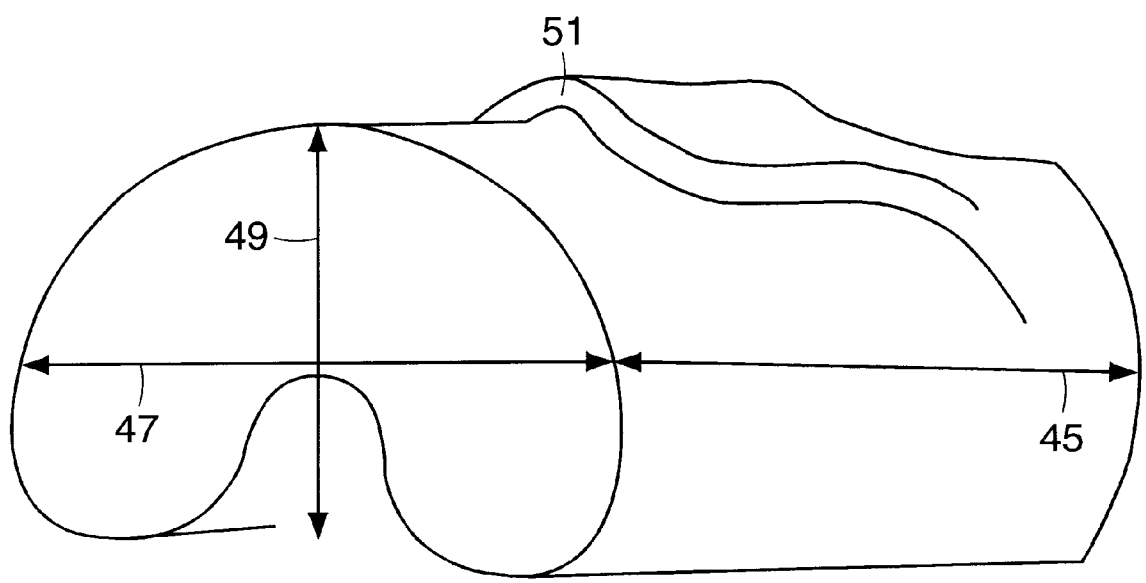
FIG. 2B is a transverse view through a device of the invention in which the expandable portion is in the collapsed or retracted position.

In another embodiment of the invention, shown in FIG. 2a, the preferred device comprises a U-shaped member having a horizontal axis 47 a longitudinal axis 45, a vertical axis 49 and having an expandable portion. The concavity of the "U" is located on the anterior side of the device adjacent to the pelvic floor, thereby permitting the urethra or other structures of the pelvic canal to remain unimpeded in the concavity of the device. In this embodiment, deflation of the device is not required for urination. Other member embodiments are contemplated including, but not limited to, tube, disc, rectangular, and ring shapes. The expandable portion comprises a deflatable, flexible, deformable, or retractable ridge having variable length, width, and depth, capable of assuming two positions. In the first position, shown in FIG. 2b, the expanded portion 51 is deflated, deformed, flexed, or retracted allowing intra-vaginal insertion or removal of the device through the vaginal sphincter. In the second position, the expanded portion extends outwardly from the member. In one embodiment the expandable portion 51 extends toward the patient's spine causing the recto-vaginal septum to deviate posteriorly, thereby compressing the lumen of the terminal rectum dorso-ventrally. In still another embodiment, the expandable portion extends anteriorly towards the pelvic floor causing the member of the device to deviate posteriorly thereby displacing the recto-vaginal septum into the rectal canal, compressing the lumen of the terminal rectum dorso-ventrally.

The device comprises single or multiple, solid or hollow expandable portions extending in a plurality of planes. The invention contemplates an expandable portion comprising a plurality of contours in transverse section including but not limited to triangular, rectangular, tubular, and ovals shapes. The expandable portion and member are constructed of flexible materials or flexible materials that accommodate increased pressure caused by inflation or expulsion of gas, or both. The device comprises material including, but not limited to rubber, plastic and polyurethane.

Other features of the device will become apparent upon consideration of the foregoing description. Accordingly, the invention is limited only by the scope of the appended claims.

I claim:

1. An intra-vaginal device for preventing unwanted expulsion of fecal matter, comprising;
   a flexible U-shaped member, capable of insertion in a vagina, having a posterior portion with an expandable member attached thereto for contacting the recto-vaginal septum,
   said expandable member capable of assuming either a first unexpanded position or a second expanded position, wherein the second position of said expandable member causes deviation of the recto-vaginal septum, thereby to simultaneously occlude the rectal canal and to permit urination.

2. The device of claim 1 wherein said portion is an expandable sheath.

3. The device of claim 2 wherein said member is a tubular member.

4. The device of claim 1 wherein said portion comprises a flexible material.

5. The device of claim 1 wherein said member comprises material selected from the group consisting of plastic, rubber, and polyurethane.

6. The device of claim 1 wherein bilaterally extending wings are attached to an end of said member.

7. An intra-vaginal device for preventing unwanted expulsion of fecal material, comprising a U-shaped member having a longitudinal axis and a horizontal axis, and being capable of substantially conforming to a cross-section of the vaginal cavity,
   said member having an posterior portion with an expandable member attached thereto for contacting the recto-vaginal septum, said expandable member capable of assuming a first unexpanded position or a second expanded position, wherein the second position of said expandable member causes deviation of the recto-vaginal septum
   to simultaneously occlude the rectal canal and to permit urination.

8. The device of claim 7 wherein said member comprises material selected from the group consisting of plastic, rubber, and polyurethane.

9. The device of claim 7 further comprising means for expanding said expandable member.

10. The device of claim 7 wherein bilaterally extending wings are attached to an end of said member.

11. An intra-vaginal device for preventing unwanted expulsion of fecal material, comprising:
   a tubular U-sloped member having a closed end and an open end, and a posterior portion with an expandable sheath attached thereto for contacting the rectum;
   said expandable sheath defines an enclosed space,
   wherein said posterior portion comprises at least one opening communicating between said enclosed space and an internal cavity defined by said tubular member, and wherein said expandable sheath attached on said posterior portion of said tubular member is capable of assuming a first unexpanded position or a second expanded position, wherein said second position of said expandable sheath causes deviation of the recto-vaginal septum, thereby to simultaneously occlude the rectal canal and to permit urination; and,
   a valve connected to said open end, said valve being capable of receiving a pump for inflating said expandable sheath.

12. The device of claim 11 wherein said valve is a locking valve for prevention of backflow of material introduced into said member.

13. The device of claim 11 wherein said member comprises material selected from the group consisting of plastic, rubber, and polyurethane.

14. The device of claim 11 wherein bilaterally extending wings are attached to an end of said member.

15. The device of claim 11 further comprises a pump for inflating said sheath.

16. The device of claim 15 wherein said pump is a syringe.

* * * * *

UNITED STATES PATENT AND TRADEMARK OFFICE
CERTIFICATE OF CORRECTION

PATENT NO. : 6,013,023
DATED : January 11, 2000
INVENTOR(S) : Klingenstein

It is certified that error appears in the above-identified patent and that said Letters Patent is hereby corrected as shown below:

On the Title Page,
Box [63], under "Related U.S. Application Data," delete "[63] Continuation of application No. 08/791,282, Jan. 30, 1997" and replace with -- [63] Continuation-in-part of application No. 08/791,282, Jan. 30, 1997 --.

Signed and Sealed this

Twenty-fourth Day of July, 2001

Attest:

*Attesting Officer*

NICHOLAS P. GODICI
*Acting Director of the United States Patent and Trademark Office*